United States Patent [19]

Damadian

[11] 4,354,499

[45] Oct. 19, 1982

[54] APPARATUS AND METHOD FOR NUCLEAR MAGNETIC RESONANCE SCANNING AND MAPPING

[76] Inventor: Raymond V. Damadian, 64 Shorthill Rd., Forest Hills, N.Y. 11375

[21] Appl. No.: 961,858

[22] Filed: Nov. 20, 1978

[51] Int. Cl.³ ............................................. A61B 5/05
[52] U.S. Cl. .................................... 128/653; 324/309
[58] Field of Search ................ 128/632, 653; 324/309

[56] References Cited

U.S. PATENT DOCUMENTS 3,932,805  1/1976  Abe et al. ............................ 324/309
4,021,726  5/1977  Carroway et al. ................... 324/309

FOREIGN PATENT DOCUMENTS 2716492  11/1977  Fed. Rep. of Germany ...... 324/309

OTHER PUBLICATIONS

*Physiological Chem. & Physics*, vol. 9, No. 1, 1977, pp. 97-108.
*Hospital Practice*, Jul. 1977, pp. 63-70.
Lauterbur, P. C., Paper Pres. at 5th Intern. Symp. on Mag. Resonance, Bombay, India, Jan. 1974, pp. 1-10.
Kumar, A., et al., *Journ. of Mag. Resonance*, vol. 18, No. 1, Apr. 1975, pp. 69-83.
Damadian, R., et al., *Physiol. Chem. & Physics*, No. 8, 1976, pp. 61-65.
Grannell, P. K., et al., *Phys. Med. Biol.*, (1975), vol. 20, No. 3, pp. 477-482.

*Primary Examiner*—Kyle L. Howell
*Attorney, Agent, or Firm*—Richard C. Conover

[57] ABSTRACT

An improved apparatus and method for analyzing the chemical and structural composition of a specimen including whole-body specimens which may include, for example, living mammals, utilizing nuclear magnetic resonance (NMR) techniques. A magnetic field space necessary to obtain an NMR signal characteristic of the chemical structure of the specimen is focused to provide a resonance domain of selectable size, which may then be moved in a pattern with respect to the specimen to scan the specimen.

15 Claims, 16 Drawing Figures

δ, ppm

APPARATUS AND METHOD FOR NUCLEAR MAGNETIC RESONANCE SCANNING AND MAPPING

BACKGROUND OF INVENTION

This invention relates to an improved apparatus and method of analyzing the chemical structure of a specimen utilizing nuclear magnetic resonance ("NMR") techniques. A resonance domain having a selectable size is moved in a discrete cross sectional grid pattern with respect to the specimen to scan the specimen. NMR signals are generated at discrete grid locations during scanning which signals are detected and processed to form a map showing the location and an indication of the quantitative amount of selected nuclei present at such location. By suitable rearrangement of the apparatus, sagittal and frontal sectional maps may also be produced.

This invention is an improvement of the apparatus and method described in U.S. Pat. No. 3,789,832 to Raymond V. Damadian (the '832 patent). As described in the '832 patent, it was discovered that cancerous cells had chemical structures different from normal cells. A method and apparatus were described in the '832 patent of measuring certain NMR signals produced from a specimen and comparing these signals with the NMR signals obtained from normal tissue to obtain an indication of the presence, location and degree of malignancy of cancerous tissue within the specimen.

The use of NMR techniques to analyze materials including living tissue has been an active field since the issuance of the '832 patent. For example, see "Medical Imaging by NMR" by P. Mansfield and A. A. Maudsley, British Journal of Radiology, Vol. 50, pages 188-194 (1977); "Image Formation by Nuclear Magnetic Resonance: The Sensitive-Point Method" by Waldo S. Hinshaw, Journal of Applied Physics, Vol. 47, No. 8, August, 1976; "Magnetic Resonance Zeugmatography" by Paul C. Lauterbur, Pure and Applied Chemistry, Vol. 40, No. 1-2 (1974); U.S. Pat. No. 4,015,196 to Moore et al.; and U.S. Pat. No. 3,932,805 to Abe et al.

These references include discussion of various methods of analyzing a specimen utilizing NMR techniques. All of these methods, however, have a major disadvantage in that the magnetic field for generating NMR signals cannot be focused to adjust the size of the resonance domain depending on the particular user requirements which might occur, for example, when a macroscopic scan of a specimen is desired instead of a microscopic scan.

The inventor here has published several articles on the general subject of utilizing field focusing NMR techniques. See "Tumor Imaging In A Live Animal By Field Focusing NMR (FONAR)", Physiological Chemistry and Physics, Vol. 8, pages 61-65, (1976); "Field Focusing Nuclear Magnetic Resonance (FONAR): Visualization of a Tumor in a Live Animal", Science, Vol. 194, pages 1430-1432 (Dec. 27, 1976); "Nuclear Magnetic Resonance: A Noninvasive Approach to Cancer", Hospital Practice, pages 63-70 (July, 1977) and "NMR in Cancer: XVI. Fonar Image of the Live Human Body" by R. Damadian et al., Physiological Chemistry and Physics, Vol. 9, No. 1 (1977). There has also appeared an article "Damadian's Super Magnet and How He Hopes To Use It To Detect Cancer" by Susan Renner-Smith in Popular Science, pages 76-79, 120 (December, 1977).

SUMMARY OF INVENTION

In its broad aspects, the present invention overcomes the disadvantages of the prior art by providing a method and apparatus for producing a resonance domain of selectable size, which may be utilized in whole body scanning of a live specimen such as a human. When oscillating magnetic radiation is directed to the resonance domain NMR signals are generated characteristic of the structure of selected nuclei within the resonance domain. These NMR signals are detected, processed and displayed to provide a user with information for analyzing the chemical structure of the specimen within the resonance domain. Apparatus is provided to move the resonance domain in a cross sectional grid pattern with respect to the specimen to obtain an indication of the composition of a cross section of the specimen. Thus an improved method and apparatus are provided for noninvasively analyzing the chemical structure of a cross section of a specimen including, for example, a live mammal such as a human.

The present invention is particularly useful in cancer detection, though its use is not limited to cancer. The invention expected to be used effectively whenever diseased tissue is chemically different from normal tissue.

BRIEF DESCRIPTION OF THE DRAWINGS

In order that the invention may be clearly understood and readily carried into effect, several preferred embodiments will now be described, by way of example only, with reference to the accompanying drawings wherein:

FIG. 8A is a sectional schematic diagram of transmitter coils utilized in the embodiment shown in FIG. 8 along the section line A—A in FIG. 8.

DESCRIPTION OF PREFERRED EMBODIMENT

Figure 1:
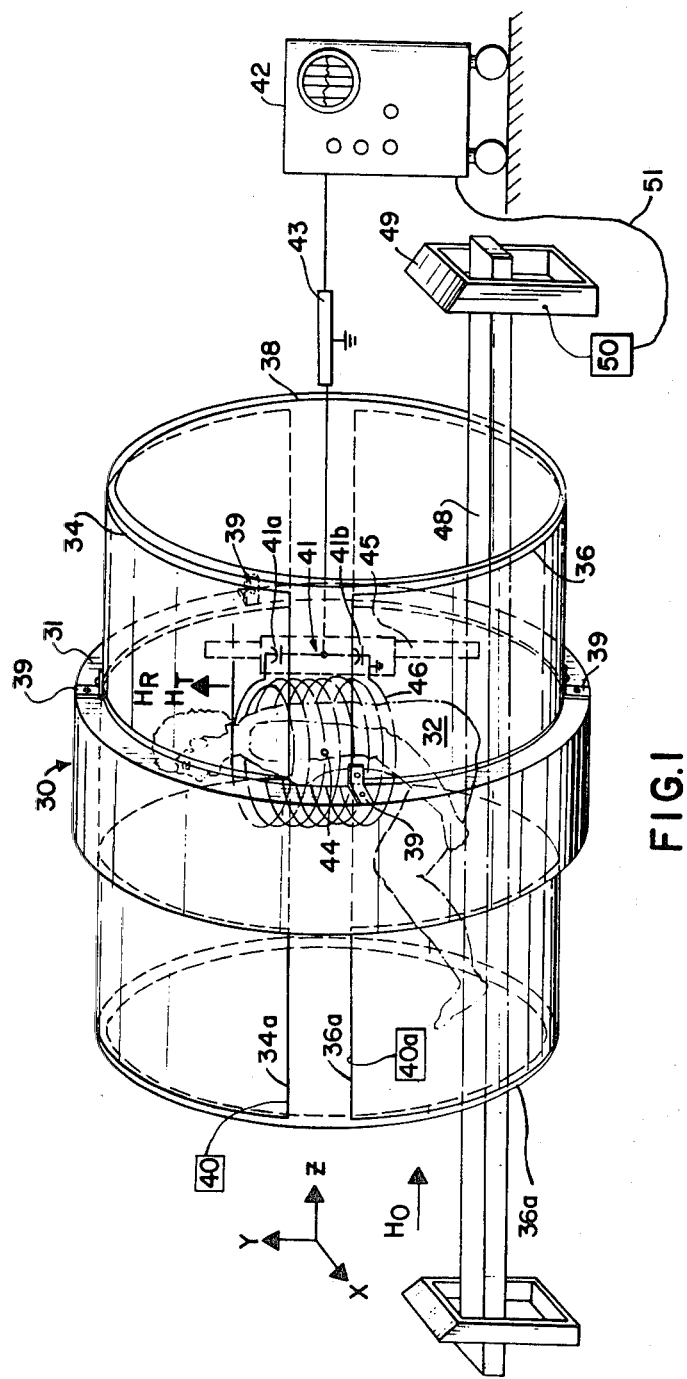
FIG. 1 is a schematic diagram of one embodiment for analyzing the chemical structure of a specimen, which as shown here may include a human.

Apparatus for analyzing the chemical structure of a cross section of a live specimen is shown in FIG. 1. A doughnut shaped magnet 30 preferably superconducting, but which may be a copper wound ambient temperature electromagnet, having a frame 31 provides a primary static magnetic field for aligning the nuclei in specimen 32, in the direction $H_o$ as shown in FIG. 1. The specimen 32 may be a human as shown in FIG. 1. Two pairs of field focusing coils 34, 34a, and 36, 36a provide a focusing static magnetic field used to adjust the primary static magnetic field configuration within the interior of the doughnut shaped magnet 30.

Figure 2:
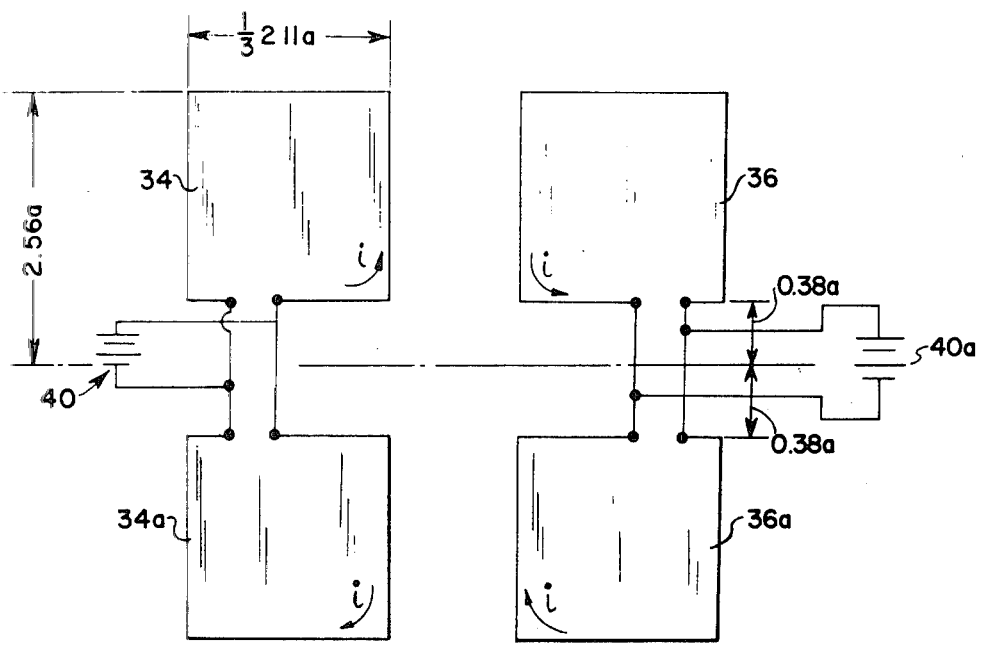
FIG. 2 is a schematic diagram of field focusing coils used in the embodiment shown in FIG. 1.
Figure 3:
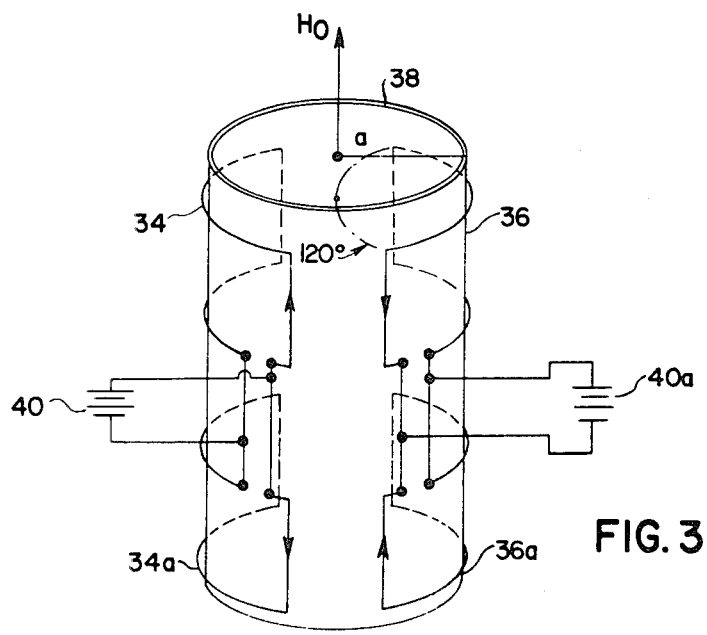
FIG. 3 is a schematic diagram of the field focusing coils shown in FIG. 2 mounted on a cylindrical form.

Field focusing coils 34, 34a, and 36, 36a are formed as shown in FIGS. 2 and 3. The coils are wound on a planar surface as shown schematically in FIG. 2. The dimensions of the field focusing coils 34, 34a, and 36, 36a are shown in FIG. 2 where "a" is the interior radius of the doughnut shaped magnet 30. The field focusing coils 34, 34a, and 36, 36a are then placed on a cylindrical form 38 which may for example be constituted of a transparent material as shown in FIG. 3. The form 38 is then placed in the interior of the doughnut shaped magnet 30 as shown in FIG. 1 and secured to the frame 31 by brackets 39.

The primary static magnetic field configuration within the doughnut shaped magnet 30 alone is well known in the art. The amplitude of the static magnetic field in the $H_o$ direction is saddle shaped with a saddle point at the origin of magnet 30. The field focusing coils 34, 34a, and 36, 36a were chosen so that when D.C. current is applied to the four field focusing coils 34, 34a, and 36, 36a in the direction as shown in FIG. 2. by D.C. sources 40, 40a, a saddle shaped static magnetic field in the direction $H_o$ is superimposed upon the saddle shaped static magnetic field provided by magnet 30 with the saddle points coinciding at the origin of magnet 30 to form a resulting static magnetic field space in the interior of magnet 30. The current level of the two D.C. sources, 40 and 40a, may be varied to adjust the sharpness of the saddle point provided by the field focusing coils 34, 34a, and 36, 36a.

The region surrounding the coincident saddle points at the origin of magnet 30 is a region of relatively uniform field strength in the direction $H_o$. Since the sharpness of the peak at the saddle point provided by field focusing coils 34, 34a, and 36, 36a is adjustable, the region of substantially uniform field strength is also adjustable. Thus when this peak is broadened, the region of relatively uniform field strength is made larger and when the peak is made sharper the region is made smaller. This region is the resonance domain 44 in which NMR conditions will be satisfied for selected nuclei as will be described later. This region of substantially uniform field strength, the resonance domain 44, is defined as that volume where the magnetic field gradient is less than 3.9 gauss/cm.

In equipment which has been built for analyzing mammals, the strength of the static magnetic field in the direction $H_o$ at the origin of the magnet 30 is approximately 500 gauss where the operating frequency is 10 MHz for protons and the D.C. sources 40 and 40a are each providing approximately 20 amperes. The size of the resonance domain 44 is dependent upon the current supplied by D.C. sources 40 and 40a. With each of the D.C. sources 40 and 40a providing 20 amperes of current, the resonance domain 44 has a volume of approximately 1 mm$^3$. In this example, the resonance domain is relatively small. By decreasing the current from D.C. sources 40 and 40a to 10 amperes, the size of the measuring volume is increased to approximately 6 mm$^3$.

Nuclear magnetic resonance conditions must exist before NMR signals are generated. The nuclear magnetic resonance conditions are described according to the well known equation:

$$\omega_o = |H_o|\gamma \tag{1}$$

where:
$\omega_o$ = resonance angular frequency of the selected nuclei
$\gamma$ = gyromagnetic ratio for the selected nuclei and is a constant for the selected nuclei
$|H_o|$ = magnitude of static magnetic field in direction $H_o$ The static magnetic field in the $H_o$ direction is provided by the superconducting magnet 30 and field focusing coils 34, 34a, and 36, 36a. The resonance frequency $\omega_o$ is supplied by a conventional adjustable radio frequency oscillator such as included in the nuclear induction apparatus or NMR spectrometer 42 which was described in the '832 patent. The oscillator provides a radio frequency signal at its output terminal having a frequency which can be adjusted manually by a frequency selector. The radio frequency signal is directed to radio frequency coil 46 as shown in FIG. 1 via transmitter and receiver line 43 and conventional capacitor divider network 41. The capacitor divider network 41 includes two capacitors 41a and 41b for impedence matching the coil 46 to line 43 as is well known in the art. The coil 46 is positioned to surround the resonance domain 44 and is of a size to surround a cross section of specimen 32. In FIG. 1, a human is shown in a sitting position with the coil 46 positioned to surround the chest. The coil 46 is placed on a form (not shown) and mounted to a frame 45, shown schematically in FIG. 1, which is anchored to a translator beam 48 that will be described later.

For NMR conditions to exist the coil 46 must be positioned so that the direction of the oscillating magnetic field provided by coil 46 is orthogonal to $H_o$. Since the direction of the radio frequency magnetic field provided by coil 46 is along the longitudinal axis of the 46, the coil 46 must be positioned such that the longitudinal axis is along the "Y" axis when the patient is sitting as shown in FIG. 1. (For purposes of explanation only, throughout this specification a three dimensional space has been assigned a conventional "X", "Y" and "Z" dimensional frame of reference as shown in the drawings.) If the patient is to lie prone on the translator beam 48, in the "Z" direction, a circular coil 46 could not be used and would need to be replaced with, for example, a pair of cylindrical Helmholtz radio frequency coils, each located on opposite sides of the chest and positioned so that the direction of the radio frequency field would be in the "X" or "Y" direction.

In practice, the value of $|H_o|$ at the location of the resonance domain 44 is determined by direct measurement prior to placing a specimen or patient within the magnet 30. Since two of the variables of equation (1) are now known—namely, $\gamma$ for the selected nuclei and $|H_o|$—a user may obtain a NMR signal for selected nuclei present in the resonance domain 44 if radio frequency radiation of the proper $\omega_o$ frequency to satisfy equation (1) is directed to the resonance domain 44 in a direction orthogonal to $H_o$.

The apparatus shown in FIG. 1 is used in a pulse mode of operation to analyze a specimen. In this embodiment a pulse of radio frequency energy from the oscillator in the NMR spectrometer 42 is directed to the resonance domain 44 through the coil 46. The coil 46 is then switched to a receiver mode to detect the NMR signal, if any, produced. The detected signal is transmitted to the NMR spectrometer 42 via transmitter and receiver line 43. The NMR spectrometer 42 includes a computer and memory means for storing NMR signal parameters such as intensities and relaxation times together with the spatial coordinates of the translator beam 48.

In the analytical apparatus described in the '832 patent, the detector and transmitting coils in the '832 patent were separate coils and were positioned orthogonal to one another. In the embodiment shown in FIG. 1, the receiver coil is the same physical coil as the transmitting coil. This is another way of accomplishing the same result. The reason for this is that when radio frequency radiation is injected into the resonance domain, the magnetic moment of the selected nuclei are energized from their equilibrium states parallel to the direction of $H_o$ to a higher energy state through nuclear magnetic resonance absorption to a direction orthogonal to the direction $H_o$ when viewed in the rotating frame. When the radio frequency radiation is turned off, the energized nuclei emit a radio frequency signal as they return to their equilibrium states according to a well known equation described in the '832 patent. The orientation of the receiver or detector coil relative to the transmitter coil is immaterial so long as they are orthogonal to the $H_o$ direction. In fact, the transmitter coil and the receiver coil may be the same physical coil as is the case of the above described embodiment shown in FIG. 1. When a single coil is used a pulsed mode of operation is necessary. It should be realized, however, that a continuous mode of operation would be possible by separating the transmitter and receiving coils and orienting them orthogonal to one another and orthogonal to $H_o$.

In FIG. 1, $H_T$ designates the direction of the transmission axis and the $H_R$ designates the direction of the receiving axis.

Scanning of a cross section of the specimen 32 in the embodiment shown in FIG. 1 is accomplished by using a translator beam 48 on which the specimen 32 is placed. Drive box 49 includes motors and gears for moving the translator beam 48 in a conventional manner in an "X" direction and "Z" direction as shown in FIG. 1. The drive box 49 is automatically activated by control unit 50 in a conventional manner to move the specimen 32 with respect to the stationary resonance domain 44 in a grid pattern in a "X-Z" plane through the specimen 32. The spatial coordinates of the translator beam 48 are transmitted to the NMR spectrometer 42 as previously discussed via lead 51 connecting the control unit 50 with the NMR spectrometer 42. Thus in scanning a human specimen 32 as shown in FIG. 1, the human is moved with respect to the stationary resonance domain 44 in a grid pattern through a cross section of the human's chest. Although FIG. 1 shows apparatus for moving the specimen 32 with respect to a stationary resonance domain 44, moving the resonance domain 44 with respect to a stationary specimen 32 is also considered to be within the scope of the present invention.

EXAMPLE 1

An experiment was performed to map a cross section of a live human chest. The human was placed in the position shown in FIG. 1 with coils 46 surrounding the chest. In this measurement, hydrogen nuclei were selected to be detected. The magnet 30 was adjusted to produce 500 gauss at the origin thereof. The translator beam 48 was moved in a grid pattern so that the human was moved with respect to the resonance domain 44 in a cross sectional pattern through the 8th thoracic vertebra as shown in FIG. 5. A pictorial depiction of this cross section is shown in FIG. 4.

The frequency of the radio frequency oscillator in NMR spectrometer 42 was set to 2.18 MHz and the oscillator adjusted to provide a 10 watt pulse of radio frequency magnetic radiation over 60 microseconds and to repeat the pulse every 800 microseconds. The control unit 50 was set to move the human patient in a grid pattern in the "X-Z" plane with movement to a new grid location accomplished just prior to the transmission of the pulse of radio frequency radiation. The NMR signals generated were detected by coil 46 and transmitted via line 43 to the NMR spectrometer 42.

Figure 5:
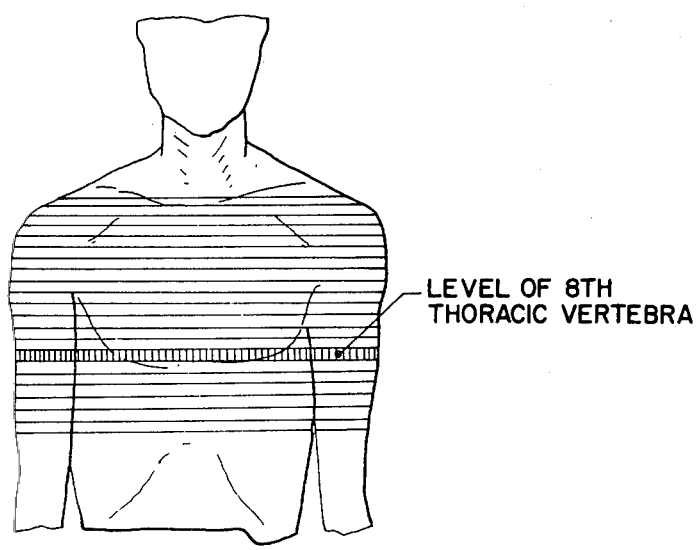
FIG. 5 is a schematic diagram showing the location of the cross section shown in FIG. 4.
Figure 6:
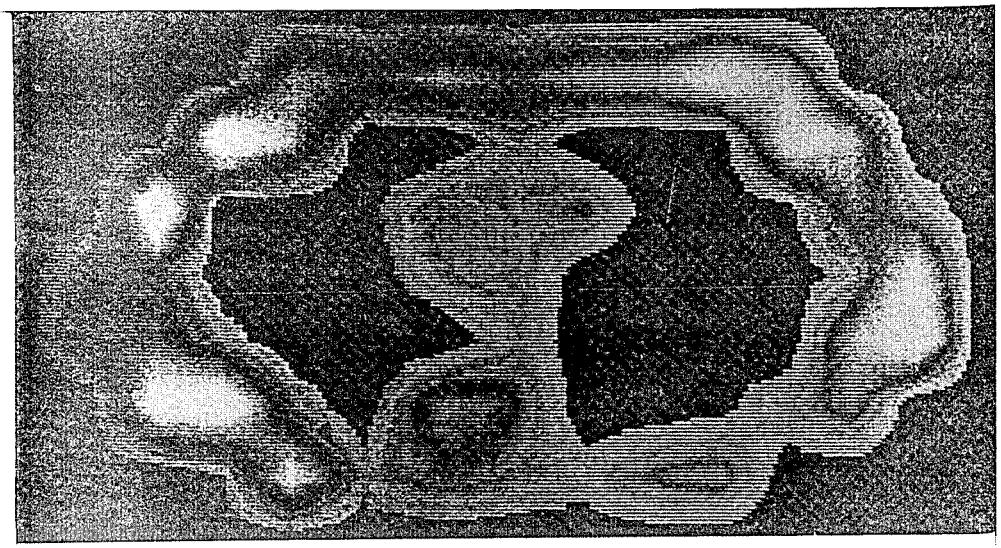
FIG. 6 is a NMR map obtained according to the principles of this invention of a cross section of a chest corresponding to the cross section shown in FIG. 4.
Figure 7:
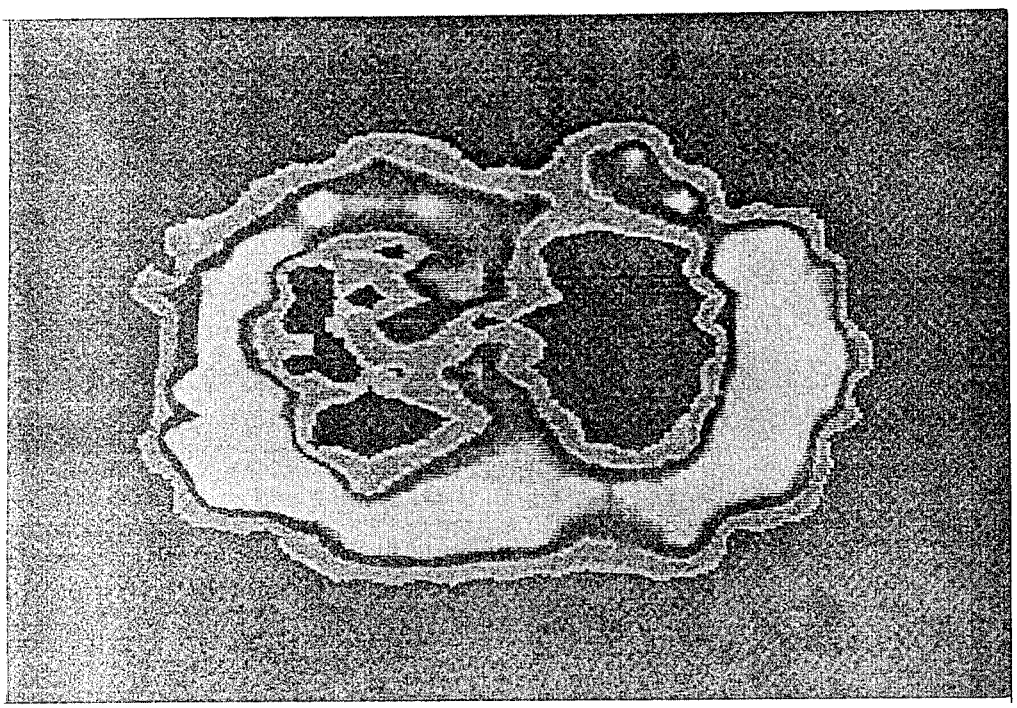
FIG. 7 is a NMR map obtained according to the principles of this invention of a cross section of a chest having a diseased left lung.

The NMR spectrometer 42 processed the NMR signals utilizing a Data General computer which was programmed to store values of NMR signal intensities received corresponding to each location on the grid. The Data General computer was also programmed so that upon completion of a cross sectional scan, a map was generated showing the NMR signal intensities for each location on the grid which map was then displayed on a video display tube in 16 colors. Each color corresponded to a different intensity, ranging from white to yellow to red to blue to black with white corresponding to maximum intensity. FIG. 6 shows a black and white photograph of the original 16 color video display. The top of the image is the anterior boundary of the chest wall. The left area is the left side of the chest looking downward. The hydrogen atom NMR signal intensity is coded with black assigned to zero signal amplitude, white assigned to signals of strongest intensities and intermediate grey scales assigned to intermediate intensities. Proceeding from the anterior to the posterior along the midline, the principal structure is the heart seen encroaching on the left full lung (black cavity). The left lung is diminished in size relative to the right lung (black cavity to right of midline), as it should be (see schematic of the human chest in FIG. 4 at the 8th thoracic level shown in FIG. 5). More posteriorly and slightly left of midline is a grey circular structure corresponding to the descending aorta.

Figure 4:
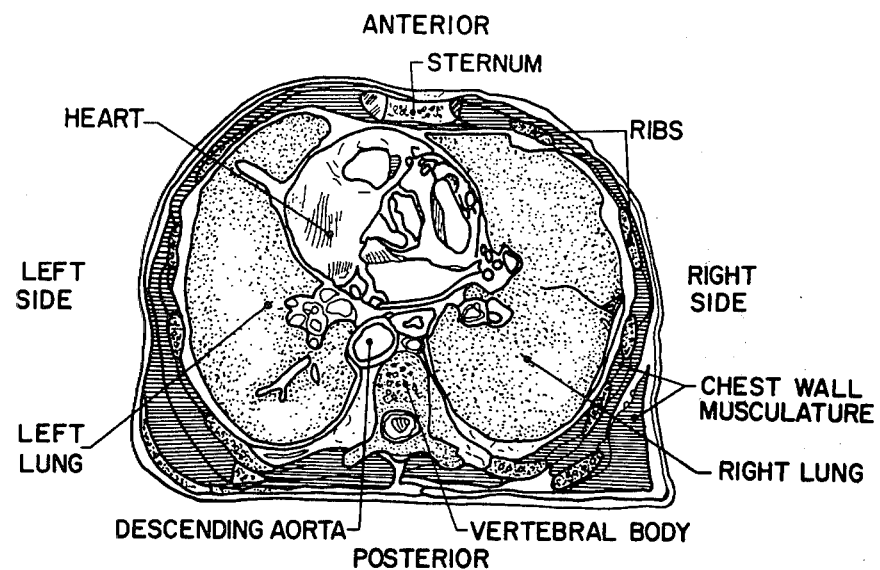
FIG. 4 is a schematic cross section of a human chest.

In the body wall, beginning at the sternum (anterior midline) and proceeding around the ellipse, alternation of high intensity (white) with intermediate intensity (grey) could correspond to alternation of intercostal muscles (high intensity) with ribs (low intensity) as shown in FIG. 4.

EXAMPLE 2

With the apparatus of FIG. 1 set up as with Experiment 1 a map was created of a cross section through the chest of a human patient having a known cancerous left lung. The black and white photograph of an original 16 color video display showing infiltration of disease into the left lung is shown in FIG. 6.

The top portion of the image in FIG. 6 is the anterior chest wall and the left side is the left side of the chest looking downward. The cancerous left lung is clearly visible.

Figure 8:
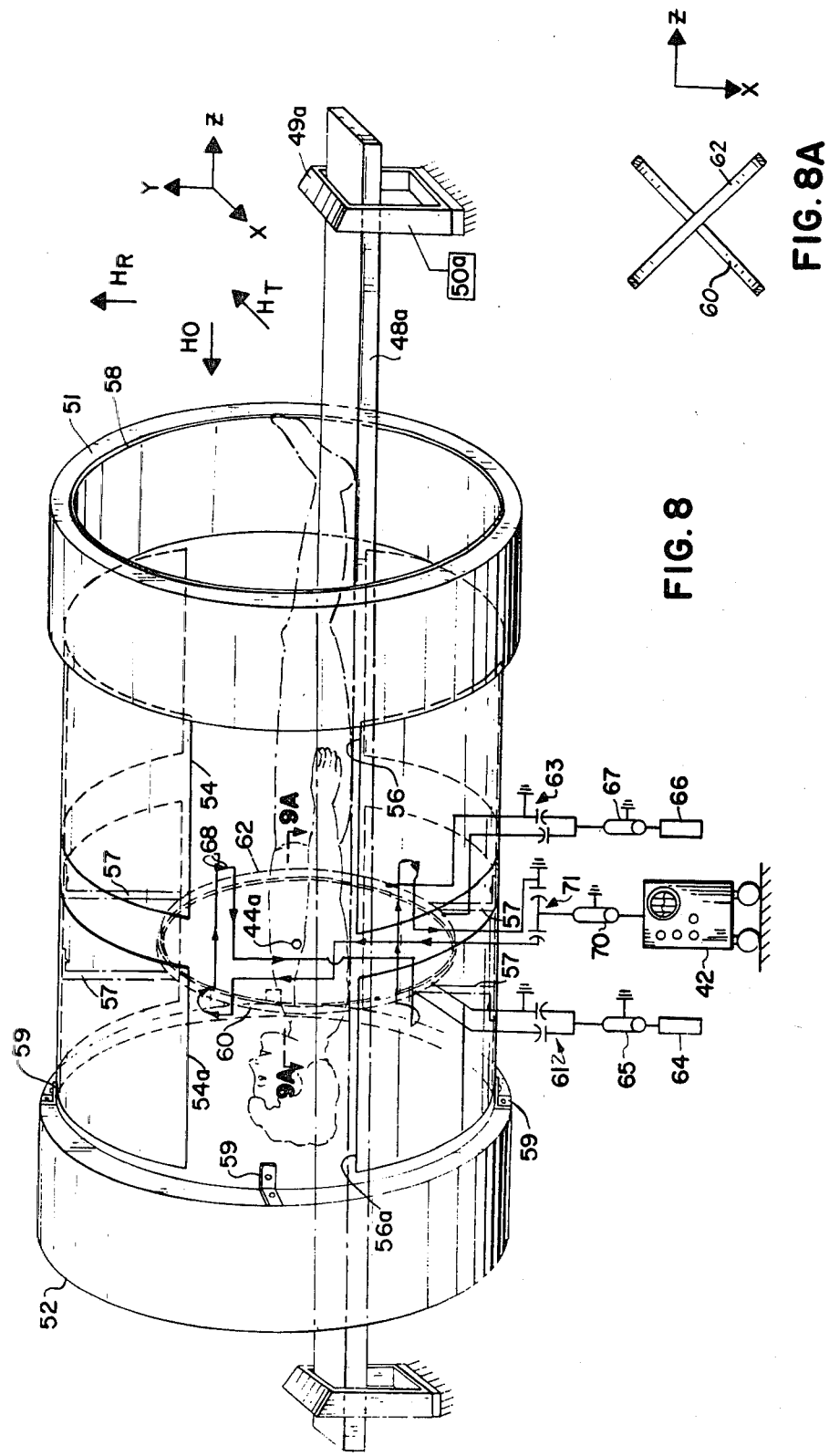
FIG. 8 is a schematic diagram of second embodiment for analyzing the composition of a specimen which again may include a human as shown here.

In a second embodiment a resonance domain 44a of selectable size is formed by the apparatus as shown in FIG. 8. In this embodiment two identical doughout shaped magnets 51 and 52, which may again be superconducting or copper wound ambient temperature magnets, are axially aligned and separated by a Helmholtz distance which distance is the radius of the magnets 51 and 52. It is well known that with this configuration, the magnetic field strength within the space between the two magnets 51 and 52 is substantially uniform. This field is the primary static magnetic field and the direction of this field $H_o$ is parallel to the "Z" axis of the magnet pair 51 and 52.

Field focusing coils 54, 54a, and 56, 56a provide the focusing static magnetic field and are used to adjust the size of measuring volume 44a as field focusing coils 34, 34a, and 36, 36a did with the first described embodiment. The field focusing coils 34, 34a, and 36, 36a respectively are as shown in FIGS. 2 and 3 except that the current in coils 54, 54a are reversed from the current in coils 34, and 34a respectively. These coils are placed on cylindrical form 58 which is attached to the frames of magnets 51 and 52 by brackets 59. It is known that when these coils are positioned in this manner, the direction of the magnetic field is along the "Z" axis and the gradient of the magnetic field strength between the field focusing coils 54, 54a, and 56, 56a along the "Y" axis is linear. Thus when the cylindrical form 58 is placed as shown in FIG. 8 coaxially aligned with the axes of the two magnets 51 and 52 the magnetic field produced by field focusing coils 34, 34a, and 36, 36a is in the $H_o$ direction with a linear gradient orthogonal to the "Z" axis.

The resulting static magnetic field produced by magnets 51 and 52 and field focusing coils 34, 34a, and 36, 36a in the direction $H_o$ is substantially uniform in the "X-Z" plane and has a linear gradient in the "Y" direction. This static magnetic field in the direction $H_o$ is in the static magnetic field necessary to establish NMR conditions according to equation (1).

Two transmitter radio frequency coils 60 and 62 are mounted to form 58 by brackets 59 and provide the radio frequency signal necessary for NMR conditions. These coils may be rectangular but are preferably circular as shown in FIG. 8 and are arranged orthogonal to one another with the line of intersection in the "Y" direction and intersecting the axes of the two magnets 51 and 52. The planes of each radio frequency coil 60 and 62 is tilted 45° with respect to the "X-Y" plane as shown in FIG. 8A which is a cross sectional top view of these coils along the section line A—A shown in FIG. 8. Radio frequency coils 60 and 62 are connected to radio frequency current sources 64 and 66 through conventional capacitor divider networks 61 and 63 and transmission lines 65 and 67. The capacitor divider networks 61 and 63 are provided to match the impedance of the coils 60 and 62 with the transmission lines 65 and 64, respectively. The alternating current in the two coils 60 and 62 are phased so that the resultant of the magnetic field vectors for the coils is orthogonal to the main magnet axis (i.e. orthogonal to "Z") and lies in the illustration shown in FIG. 8 along the "X" axis. With this arrangement the maximum amplitude of the radio frequency magnetic field is along the "Y" axis with an exponential amplitude drop off from the "Y" axis. The coils 60 and 62 thus focus the oscillating magnetic energy in a pencil beam along the "Y" axis. This pencil beam will be the source of the $\omega_o$ in equation (1) above. A separate cylindrical Helmholtz coil 68 operates as the receiver coil and has its magnetic axis perpendicular to "X" and "Z", that is along the "Y" axis in the illustration shown in FIG. 8. The receiver coil 68 is supported by supports (not shown) on a translator beam 48 and will move with the patient during scanning.

Figure 9:
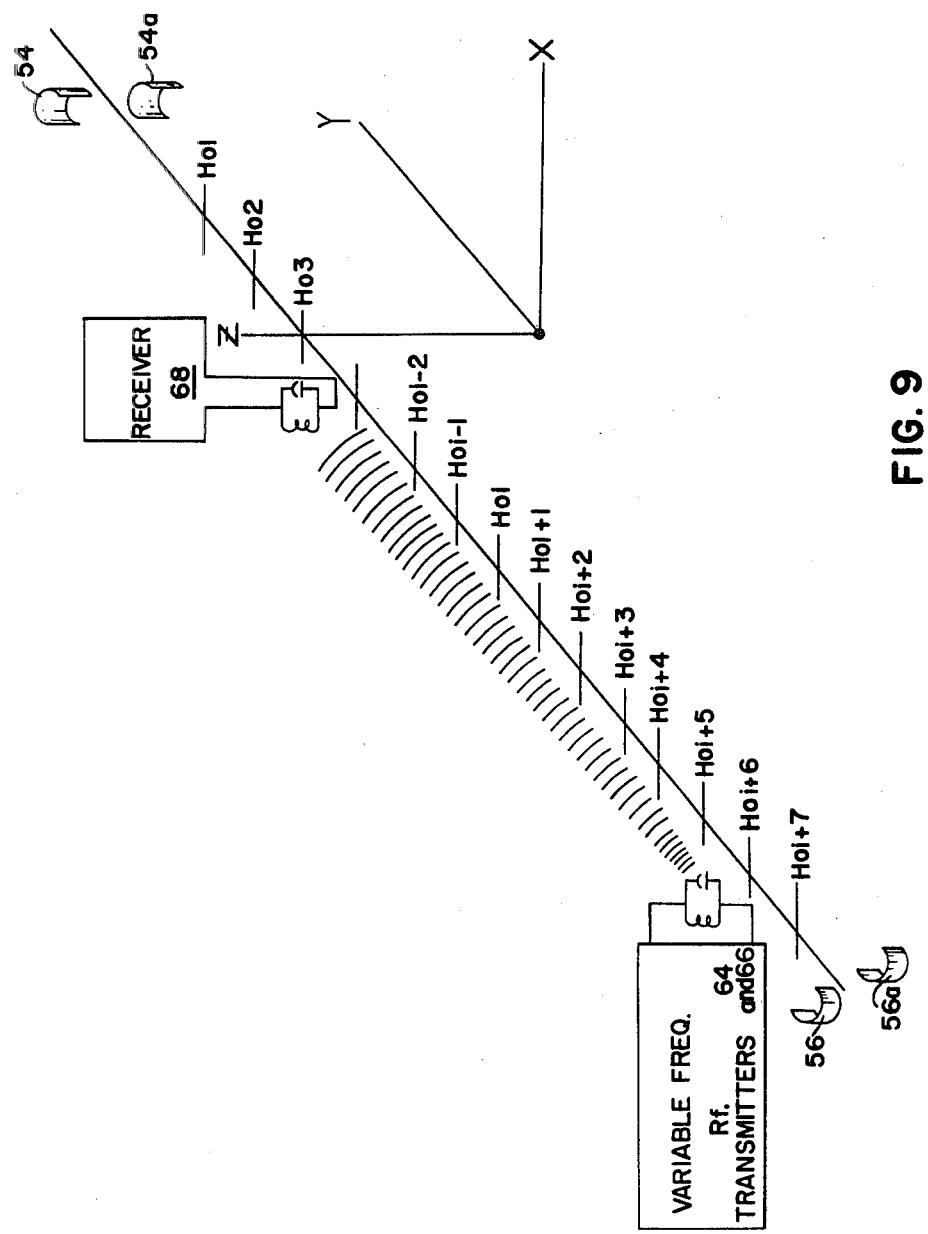
FIG. 9 is a schematic diagram useful in describing the principle of operation of the embodiment shown in FIG. 8.
Figure 10:
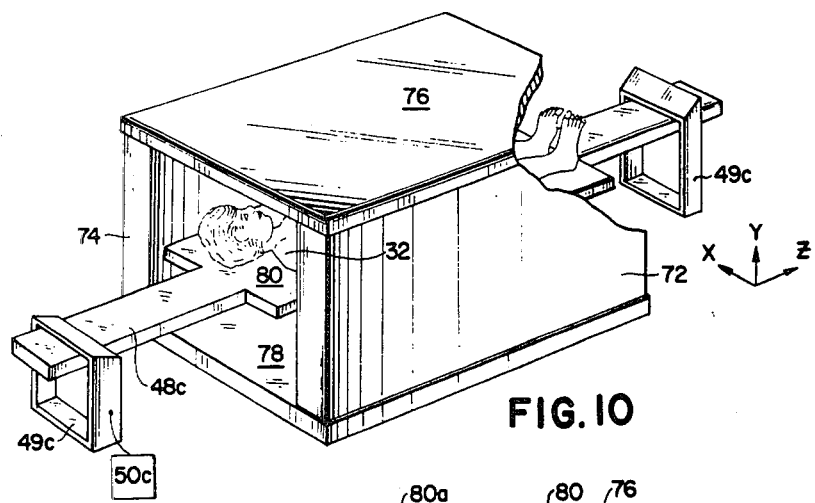
FIG. 10 is a schematic perspective diagram of a third embodiment for analyzing the composition of a specimen utilizing permanent magnets.
Figure 11:
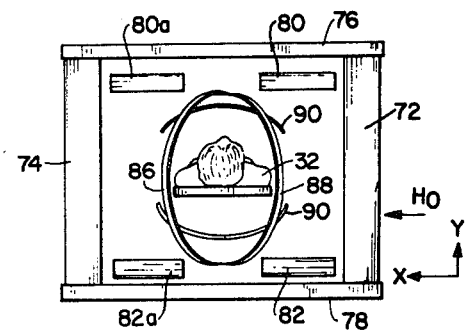
FIG. 11 is a schematic front view of the embodiment shown in FIG. 10.
Figure 12:
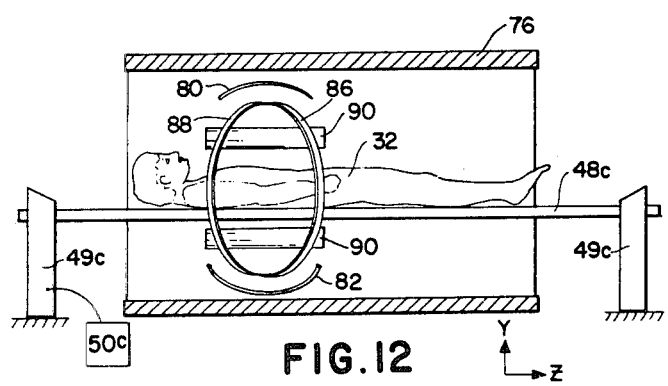
FIG. 12 is a schematic side view of the embodiment shown in FIG. 10 with one permanent magnet removed.
Figure 13:
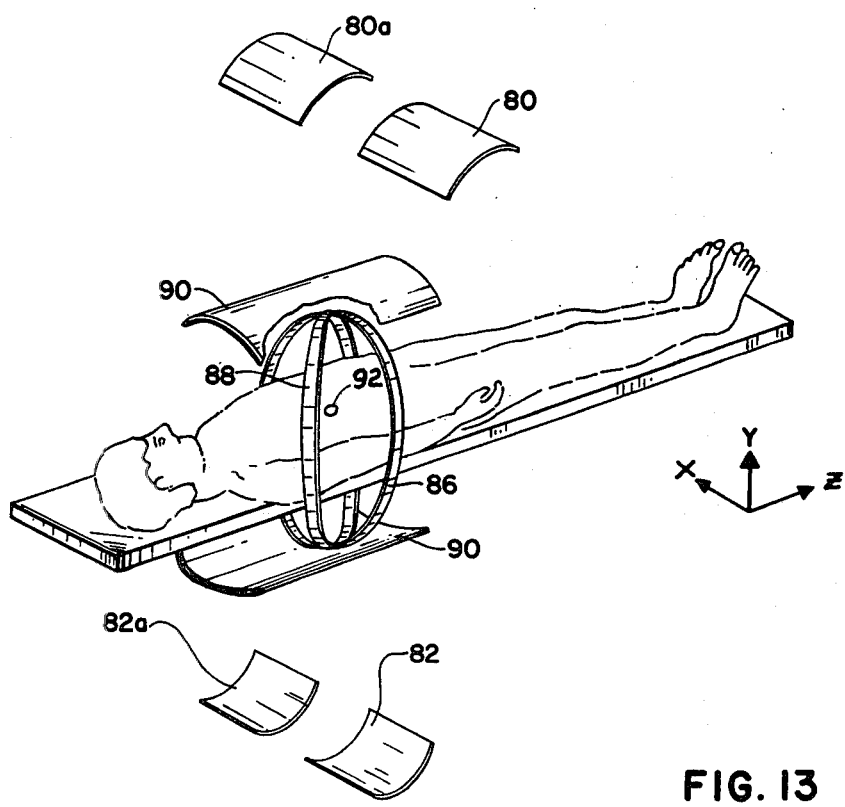
FIG. 13 is a schematic diagram of the embodiment shown in FIG. 10 showing the location of the various coils utilized in this embodiment.

Reference is now made to the schematic diagram shown in FIG. 9 to illustrate the method of operation. Scanning along the "Y" axis is accomplished by merely changing the frequency of the radio frequency magnetic field. This is possible because the $|H_o|$ value changes linearly along the "Y" axis between the two pairs of field focusing coils 54, 54a, and 56, 56a. In this embodiment, the superimposed field varies, for example, from $-0.50$ to $+0.50$ gauss between the field focusing coils 54, 54a, and 56, 56a, but the range and therefore the gradient can be made larger or smaller by varying the current in the field focusing coils 54, 54a, and 56, 56a. For a particular value $|H_o|$, for example $H_{oi}$ in FIG. 9, there is a particular frequency $\omega_{oi}$ to satisfy NMR conditions for the selected nuclei. Thus to obtain a measurement at the location where the value of $|H_o|$ is $H_{oi+1}$, the frequency of the transmitter coil is adjusted to be $\omega_{oi+1}$. By varying the frequency directed to transmitter radio frequency coils 60 and 62, means are provided for scanning a specimen along a pencil beam through the specimen. The range of $|H_o|$ values established by the field focusing coils 54, 54a, and 56, 56a along the "Y" axis is sufficiently small so that only the selected nuclei are energized when the frequency sources 64 and 66 are changed. Thus a user can be sure that when a particular $\omega_{oi}$ is used only the selected nuclei at the location $H_{oi}$ are being resonated.

The steepness of the gradient provided by field focusing coils 54, 54a, and 56, 56a determines the size of the measuring volume 44a because with a smaller gradient there is a larger region with substantially the same magnetic field strength than with a larger gradient.

To obtain a cross sectional scan of a specimen, for example a human, the human is placed on a translator beam 48a as shown in FIG. 5. The pencil scanning beam provided by transmitter coils 60 and 62 is along "Y" axis. The beam and specimen are moved incrementally along the "X" axis by a conventional drive box 48a and drive control unit 50a after a complete scan along the pencil beam along the "Y" axis is completed. Thus a cross sectional scan of a slice perpendicular to the "Z" axis in this illustration may be achieved. At each point on the cross sectional grid the detector or receiver coil 68 will detect any NMR signal generated. The intensity or any other parameter of the signal together with the corresponding position of the resonance domain 44a is stored in a computer memory located in the NMR spectrometer 42 connected to the receiver coil 68 through a transmission line 70 and capacitor divider network 71. These intensity values are later processed to form a cross sectional grid of values in an "X-Y" plane through the specimen to provide a map showing the location and intensity of the signal received at each location on the grid.

Although structure is shown in FIG. 8 for moving the specimen 32 with respect to a stationary pencil of transmitted radio frequency energy, it is considered that structure may be incorporated for rotating the field focusing coils 54, 54a, and 56, 56a; the transmitter coils 60 and 62; and the receiver coil 68 about the "Z" axis on a stepped bases after a complete scan along the pencil beam to complete a map of values utilizing a radial sweep pattern. The pencil beam would be rotated through 180° to obtain a complete cross sectional scan of a specimen. This is also considered to be within the scope of the present invention.

In addition, depending on the geometry of the specimen to be analyzed the direction of the magnetic axis of transmitter coils 60 and 62 ($H_T$) and direction of the magnetic axis of receiver coil 68 ($H_R$) in FIG. 8 may be reversed by repositioning the transmitting coils 60 and 62 and the receiving coil 68 so long as $H_T$, $H_R$ and $H_o$ are mutually orthogonal. In the particular configuration shown in FIG. 8, it is preferred that the human patient be positioned to lie on his back, since the length of the pencil beam provided by transmitter coils 60 and 62 which extends through the specimen is minimized. However, other variations are contemplated and considered to be within the scope of the invention.

A third embodiment embodying the principles of this invention is shown in FIGS. 10–13. In this embodiment the static magnetic field in the $H_o$ direction is provided by permanent magnets 76 and 78. Pole faces 72 and 74 are mounted on the magnets 76 and 78 to concentrate flux. The configuration of the static magnetic field between permanent magnets 76 and 78 is well known to be substantially uniform.

The specimen 32 to be analyzed which again may be, for example, a human is positioned on a translator beam 48c associated again with drive box 49c and control unit 50c within the space between magnets 76 and 78. Field focusing coils 80, 80a, and 82, 82a correspond to field focusing coils 54, 54a, and 56, 56a of the second embodiment shown in FIG. 8 and provide a linear gradient of the static field in the $H_o$ direction along the "Y" axis.

Transmitter coils 86 and 88 correspond to transmitter coils 60 and 62 of the embodiment shown in FIG. 8. In this embodiment, the line of intersection of the transmitter coils 86 and 88 is along the "Y" axis and each of the transmitter coils 86 and 88 are orthogonal to the other and tilted 45° to the "Y-Z" plane. The receiver coil 90 corresponds to receiver coil 68 in the embodiment shown in FIG. 8. In FIGS. 11–14, the connection of these coils to sources and the NMR spectrometer are not shown since they are the same as the embodiment shown in FIG. 8.

The apparatus shown in FIGS. 10–13 functions in the same manner as the apparatus shown in FIG. 8 and is similar to such apparatus with the exception that here permanent magnets 76 and 78 replace the Helmholtz pair of magnets 51 and 52 as was the case with the embodiment shown in FIG. 8. The magnetic directions of transmitter coils 86 and 88 ($H_T$) and the receiver coil 90 ($H_R$) are still orthogonal and both are still orthogonal to $H_o$. To accomodate a human patient, the coils had to be rearranged; however, the principle of operation in both embodiments is identical.

The direction of $H_o$ in this third embodiment is along the "X" axis instead of the "Z" axis. $H_R$ is in the "Y" direction, and $H_T$ is in the "Z" direction, thus $H_o$, $H_R$ and $H_T$ are all orthogonal to one another. A resonance domain 92 is located on a pencil beam provided by the transmitter coils 86 and 88 as was the case with the embodiment shown in FIG. 8. Since the pencil beam is located on the line of intersection of the planes of the two transmitter coils 86 and 88, the pencil beam lies along the "Y" axis.

Scanning is accomplished as with the embodiment shown in FIG. 8 by scanning along the pencil beam in the "Y" direction and translating the specimen or patient 32 in the "X" direction. This provides scanning in the "X-Y" plane. The NMR signal intensity is measured at each point on the pencil beam at each discrete position of the pencil beam with respect to the specimen. Again, the values detected are stored, processed and displayed to show a cross sectional map of the specimen showing intensities of NMR signal at each location on the cross section of the specimen.

With any of the three embodiments above described, a user may process the NMR signal obtained and determine a nuclear magnetic value which may be, for example, the intensity of the NMR signal obtained representing the degree of presence of the selected nuclei within the resonance domain; an amplitude versus frequency spectrum indicative of the atomic combinations of the selected nuclei within the resonance volume; the spin-lattice relaxation time; the spin-spin relaxation time; spin-mapping values of selected nuclei indicative of the degree of organization of the selected nuclei within the resonance domain. All of these nuclear magnetic resonance values obtained may be displayed for analysis by a user and cross sectional maps may be made. In detecting cancerous tissue in mammals it is preferred that the selected nuclei be, for example, $P^{31}$, $K^{39}$, $Na^{23}$, $H^1$, $C^{13}$, $N^{15}$, $N^{14}$ and $O^{17}$. However, this apparatus may be used in detecting and analyzing other diseases in tissue when selected nuclei in the diseased tissue has a different chemical organizational structure from the selected nuclei of normal non-diseased tissue.

In forming NMR amplitude versus frequency spectra, a pulse mode of operation may be used with the above described three embodiments wherein the transmitted pulse injected into the resonance domain has a band of frequencies. The resulting amplitude versus time NMR signal detected by the receiver coils is directed to NMR spectrometer 42 having a computer programmed to perform a Fast Fourier Transform on the data received to develop an amplitude versus frequency spectrum.

Figure 14A:
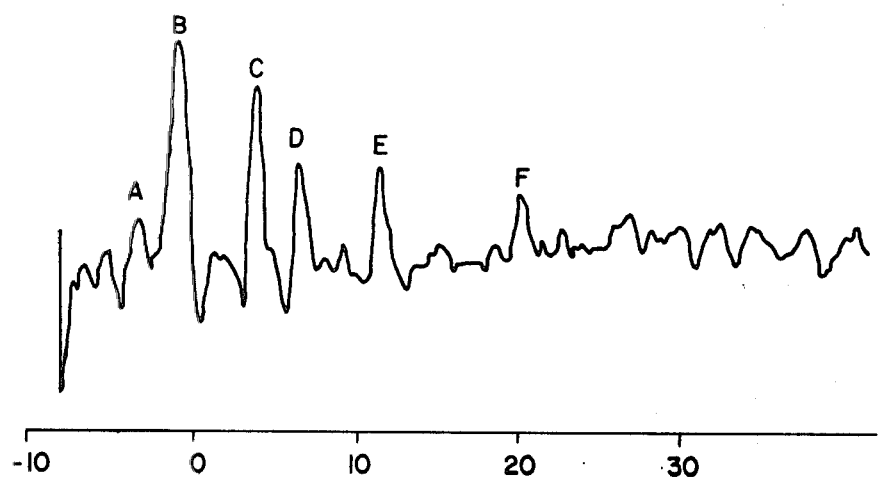
FIG. 14A is a NMR spectrum obtained from normal muscle tissue.
Figure 14B:
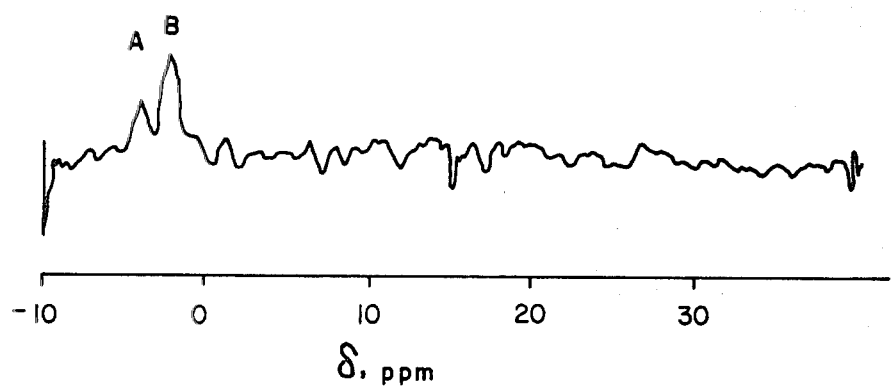
FIG. 14B is a NMR spectrum obtained from cancerous muscle tissue.

Examples of such amplitude versus frequency spectra which were obtained using the first embodiment are shown in FIGS. 14A and 14B.

EXAMPLE 3

FIG. 14A shows a $P^{31}$ NMR spectrum obtained non-invasively for normal muscle tissue and FIG. 14B shows on $P^{31}$ NMR spectrum obtained non-invasively for malignant muscle. The operating frequency of the radio frequency oscillator was 100 MHz and the bandwidth of the transmitted pulse was 5,000 Hz and from 100 MHz−1,000 Hz to 100 MHz+4,000 Hz and the pulse interval was 10 seconds. The resulting spectrum was the 256 averaged free induction decay peak positions based on the mean positions of 8 separate experiments. Each peak is the resonance from phosphorus for a different phosphorus containing molecule except in the case of adenosine tri-phosphate (ATP) where three resonances (Peaks D, E, and F in FIG. 15A) are seen for the molecule, one for each of three phosphates. Peak A in FIGS. 14A and 14B is the phosphorus resonance of a sugar phosphate positioned at −3.9 ppm in normal muscle and −4.3 ppm in malignant muscle (a difference of 40 Hz at the operating frequency of 100 MHz). Ppm is an abbreviation for parts per million and here is used to locate the frequency positions of peaks with respect to the operating frequency. One ppm corresponds to a frequency 100 Hz above the operating frequency of 100 MHz and −1 ppm corresponds to a frequency 100 Hz less than the operating frequency 100 MHz. Peak B in FIGS. 14A and 14B is the phosphorus resonance for the inorganic salts of phosphorus positioned at −1.7 ppm in normal muscle and −2.4 ppm in malignant muscle (a difference of 70 Hz). Peak C in FIG. 14A is creatine phosphate (absent in cancer), and Peaks D, E, F in FIG. 14A are the three phosphates of ATP (absent in cancer). Thus by noting the absence of certain peaks and the shift of certain peaks in a NMR spectrum obtained for tissue located within the resonance domain as compared with a NMR spectrum for malignant tissue, malignant tissue may be detected and located non-invasively.

Depending on the physical constraints caused by the geometry of the specimen to be measured, the receiver coil in all three embodiments may be a circular type coil if it can surround the specimen or be a split cylindrical Helmholtz coil if it is not practical to physically position the coil around the specimen.

Furthermore, in all three embodiments, the transmitter and receiver coils may be combined provided a pulse mode of operation is utilized as explained above in conjunction with the first embodiment.

All such variations are considered to be within the scope of the present invention.

A continuous mode of operation could also be used with the three embodiments described. However, in this mode of operation, separate transmitter and receiver coils are required which by necessity must be orthogonal to the direction $H_o$ of the static magnetic field. In the continuous mode or high resolution mode, the transmitter operates continuously as either its frequency is gradually varied or the strength of the static magnetic field in the $H_o$ direction is varied. Under these conditions and in a specimen where the selected nuclei (for example, hydrogen) exist in a variety of combinations with other atoms, the different combinations would be seen as resonance peaks. See for example FIGS. 14A and 14B. Each resonance peak represents a different wavelength for NMR absorption and is caused by the fact that different atomic combinations with the selected nuclei alter the configuration of the electron cloud surrounding the nucleus and consequently the net magnetic moment of the electron cloud. Thus, the frequency at which resonance occurs also varies with the various combinations of other nuclei with the selected nuclei. The different resonant frequencies appear as resonance peaks on an amplitude versus frequency spectrum.

As described above in conjunction with Example 3, an amplitude versus frequency spectrum can also be obtained in the pulse mode by transmitting a pulse of a predetermined bandwidth to the resonance domain; detecting the resulting NMR signal; and using a Fast Fourier Transform to generate the spectrum. The continuous mode obtained by varying the frequency of the transmitter with time provides a method of obtaining an amplitude versus frequency spectrum directly without the need of using a Fast Fourier Transform.

It should be understood that the above three embodiments could be adapted to measure NMR signals for multiple selected nuclei by, for example, mounting multiple receiver coils, one for each of the separate types of selected nuclei on top of one another. The transmitter coil would be pulsed in a timed sequence providing the necessary radio frequency signal required for NMR conditions for the first selected nuclei then the second selected nuclei, etc. Other variations such as providing electronic circuitry for detecting the transmitted signal and which would eliminate the need for multiple receiver coils is contemplated by and is within the scope of this invention. The detected NMR signals could then be processed and displayed on multiple video displays.

The present invention provides a much needed method and apparatus for determining the chemical structure of a specimen including apparatus for making a macroscopic scan or microscopic scan of the specimen. It is understood that many modifications of the structure of the preferred embodiments will occur to those skilled in the art, and it is understood that this invention is to be limited only by the scope of the following claims.

I claim:

1. A method of detecting selected nuclei within a specimen utilizing nuclear magnetic resonance pheonomenon comprising:
   (a) providing a nonuniform primary static magnetic field space;
   (b) focusing the primary static magnetic field space by a time-independent shaping of the primary static magnetic field space to provide a three dimensional resonance domain of selectable size wherein the field strength is substantially uniform;
   (c) positioning the specimen such that the resonance domain impinges on the specimen;
   (d) directing oscillating magnetic radiation to the resonance domain such that the magnetic field orientation of the oscillating magnetic radiation is orthogonal to the magnetic field orientation of the primary static magnetic field to cause a nuclear magnetic resonance signal to be generated by selected nuclei within the resonance domain;
   (e) receiving the nuclear magnetic resonance signal generated; and
   (f) processing the nuclear magnetic resonance signal to determine a nuclear magnetic resonance value directly which nuclear magnetic resonance valve represents the selected nuclei extant in the resonance domain impringing on the specimen.

2. A method of detecting selected nuclei within a specimen utilizing nuclear magnetic resonance phenomenon comprising:
   (a) providing a nonuniform primary static magnetic field having a known field configuration with a region of uniformity where the field strength is substantially uniform;
   (b) providing a time-independent focusing static magnetic field having a selectable field configuration with a region of uniformity where the field strength is substantially uniform;
   (c) superimposing the time-independent focusing static magnetic field on the primary static magnetic field such that the respective regions of uniformity coincide to produce a resulting static magnetic field having a three dimensional resonance domain located within a region where the regions of uniformity coincide, the field strength of the resulting static magnetic field within the resonance domain being substantially uniform;

(d) selecting the field configuration of the time-independent focusing static magnetic field to adjust the size of the resonance domain;

(e) positioning the specimen such that the resonance domain impinges on the specimen;

(f) directing oscillating magnetic radiation to the resonance domain such that the magnetic field orientation of the oscillating magnetic radiation is orthogonal to the magnetic field orientation of the resulting static magnetic field to cause a nuclear magnetic resonance signal to be generated;

(g) receiving the nuclear magnetic resonance signal generated; and (h) processing the signal to determine a nuclear magnetic resonance value directly which nuclear magnetic resonance valve represents the selected nuclei extant in the resonance domain within the specimen.

3. The method according to claim 2 wherein the field configuration of the primary static magnetic field has a saddle shaped gradient with the region of uniformity at the saddle point and the focusing static magnetic field has an adjustable saddle shaped gradient with the region of uniformity at the saddle point and wherein the size of the resonance domain is adjusted by changing the gradient of the focusing static magnetic field as it approaches its saddle point.

4. The method according to claim 2 wherein the oscillating magnetic radiation is directed to the resonance domain on a periodic basis and further including the step of repositioning the specimen after a nuclear magnetic resonance signal has been received such that a different portion of the specimen coincides with the resonance domain whereby scanning of the specimen may be accomplished.

5. The method according to claim 4 wherein the specimen is moved in a planar grid pattern across a cross section of the specimen such that a grid of nuclear magnetic resonance values is obtained for the cross section of the specimen.

6. The method according to claim 5 further including the step of displaying the grid of nuclear magnetic resonance values to provide a visual image of the grid.

7. The method according to claim 2 wherein a doughnut shaped superconducting magnet is utilized for providing the primary static magnetic field space and wherein the specimen is positioned within the interior space of the doughnut shaped superconducting magnet.

8. The method according to claim 7 wherein field focusing coils are used to provide the focusing static magnetic field.

9. The method according to claim 2 wherein the specimen includes a live mammal and the nuclear magnetic values may include intensitites of nuclear magnetic resonance signals received, spin-spin relaxation time, spin-lattice relaxation times, spin-mapping values, and amplitude versus frequency spectra.

10. The method according to claim 2 wherein the selected nuclei may be selected from $P^{31}$, $K^{39}$, $Na^{23}$, $H^1$, $C^{13}$, $N^{15}$, $N^{14}$ or $O^{17}$.

11. Nuclear magnetic induction apparatus for detecting selected nuclei within a specimen comprising:
(a) means for providing a nonuniform primary static magnetic field space;
(b) means for focusing the primary static magnetic field space by a time-independent shaping of the primary magnetic field space to provide a three dimensional resonance domain of selectable size wherein the field strength is substantially uniform;
(c) means for positioning the specimen such that the resonance domain impinges on the specimen;
(d) means for directing oscillating magnetic radiation to the resonance domain such that the magnetic field orientation of the oscillating magnetic radiation is orthogonal to the magnetic field orientation of the primary static magnetic field to cause a nuclear magnetic signal to be generated by selected nuclei within the resonance domain;
(e) means for receiving the nuclear magnetic resonance signal generated; and
(f) means for processing the nuclear magnetic resonance signal to determine a nuclear magnetic resonance value directly which nuclear magnetic resonance value represents the selected nuclei extant in the resonance domain impinging on the specimen.

12. Nuclear magnetic induction apparatus for detecting the selected nuclei within a specimen comprising:
(a) means for providing a nonuniform primary static magnetic field having a known field configuration with a region of uniformity where the field strength is substantially uniform;
(b) means for providing a time-independent focusing static magnetic field having a selectable field configuration with a region of uniformity where the field strength is substantially uniform;
(c) superimposing the time-independent focusing static magnetic field upon the primary static magnetic field such that the respective regions of uniformity coincide to produce a resulting static magnetic field having a three dimensional resonance domain located within a region where the regions of uniformity coincide, the field strength of the resulting static magnetic field within the resonance domain being substantially uniform;
(d) means for selecting the field configuration of the time-independent focusing static magnetic field to adjust the size of the resonance domain;
(e) means for positioning the specimen such that the resonance domain impinges on the specimen;
(f) means for directing oscillating magnetic radiation to the resonance domain such that the magnetic field orientation of the oscillating magnetic radiation is orthogonal to the magnetic field orientation of the resulting magnetic field to cause a nuclear magnetic resonance signal to be generated;
(g) receiving the nuclear magnetic signal generated; and
(h) processing the signal to determine a nuclear magnetic resonance value directly which nuclear magnetic resonance value represents the selected nuclei extant in the resonance domain within the specimen.

13. The apparatus according to claim 12 wherein the means for providing oscillating magnetic radiation is actuated on a periodic basis and further includes means for repositioning the specimen with respect to the resonance domain after a nuclear magnetic resonance signal has been received such that a different portion of the specimen coincides with the resonance domain whereby scanning of the specimen may be accomplished.

14. The apparatus according to claim 12 wherein the means for providing a primary static magnetic field comprises a doughnut shaped superconducting magnet.

15. The apparatus according to claim 12 wherein the means for providing a focusing static magnetic field comprises field focusing coils.

* * * * *